United States Patent [19]
Mori et al.

[11] Patent Number: 4,917,821
[45] Date of Patent: Apr. 17, 1990

[54] OPTICALLY ACTIVE MESOMORPHIC COMPOUND AND LIQUID CRYSTAL COMPOSITION CONTAINING SAME

[75] Inventors: Shosei Mori; Kenji Shinjo, both of Atsugi; Takashi Iwaki, Isehara, all of Japan

[73] Assignee: Canon Kabushiki Kaisha, Tokyo, Japan

[21] Appl. No.: 268,265

[22] Filed: Nov. 7, 1988

[30] Foreign Application Priority Data

Nov. 9, 1987 [JP] Japan .................. 62-281038

[51] Int. Cl.$^4$ .................. G02F 1/13; C09K 19/30; C07C 69/76; C07C 69/74
[52] U.S. Cl. .................. 252/299.63; 252/299.01; 252/299.67; 350/350 S; 558/257; 560/55
[58] Field of Search .................. 252/299.01, 299.63, 252/299.67; 350/350 S; 558/257; 560/17, 18, 9, 64, 61, 55, 1

[56] References Cited

U.S. PATENT DOCUMENTS

| | | | |
|---|---|---|---|
| 4,576,732 | 3/1986 | Isogai et al. | 252/299.67 |
| 4,596,667 | 6/1986 | Inuka et al. | 252/299.63 |
| 4,613,209 | 9/1986 | Goodby et al. | 252/299.65 |
| 4,728,458 | 3/1988 | Higuchi et al. | 252/299.65 |
| 4,798,680 | 1/1989 | Nohira et al. | 252/299.01 |
| 4,834,904 | 5/1989 | Krause | 252/299.01 |

FOREIGN PATENT DOCUMENTS

| | | | |
|---|---|---|---|
| 237007 | 9/1987 | European Pat. Off. | 252/299.63 |
| 255962 | 2/1988 | European Pat. Off. | |
| 267585 | 5/1988 | European Pat. Off. | 252/299.01 |
| 63-22042 | 1/1988 | Japan | 252/299.63 |
| 63-137986 | 6/1988 | Japan | 252/299.63 |
| 06373 | 11/1986 | PCT Int'l Appl. | |

Primary Examiner—Teddy S. Gron
Attorney, Agent, or Firm—Fitzpatrick, Cella, Harper & Scinto

[57] ABSTRACT

An optically active mesomorphic compound represented by the formula:

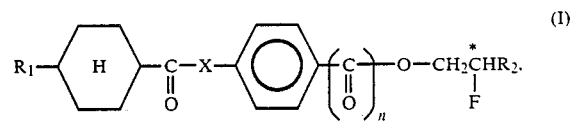

wherein $R_1$ denotes an alkyl group having 1–16 carbon atoms; $R_2$ denotes an alkyl group having 1–18 carbon atoms; C* is an asymmetric carbon atom; X is an oxygen atom or sulfur atom; and n is 0 or 1. The optically active mesomorphic compound, when included as a component, provides a ferro-electric liquid crystal composition showing an improved field response characteristic.

41 Claims, No Drawings

OPTICALLY ACTIVE MESOMORPHIC COMPOUND AND LIQUID CRYSTAL COMPOSITION CONTAINING SAME

FIELD OF THE INVENTION AND RELATED ART

The present invention relates to a novel mesomorphic compound, a liquid crystal composition containing the same and a liquid crystal device using the liquid crystal composition.

There has been a well known type of liquid crystal devices using TN (twisted nematic) type liquid crystals as shown, for example, in "Voltage-Dependent Optical Activity of a Twisted Nematic Liquid Crystal" by M. Schadt and W. Helfrich, Applied Physics Letters, Vol. 18, No. 4 (Feb. 15, 1971), pp. 127–128. In this type of liquid crystal devices, the number of picture elements have been restricted, because there is a problem that a crosstalk phenomenon occurs when a device of a matrix electrode structure with a high density of picture elements is driven according to a multiplexing driving scheme. Further, their uses for display have been limited because of slow electric field response and poor visual angle characteristics.

As another type of liquid crystal device, there has been known one comprising a plurality of picture elements each connected to and subject to switching by a thin film transistor as a switching element. This type of liquid crystal device, however, is accompanied with problems such that production of thin film transistors on a substrate is very complicated, and production of a display device with a large picture area or screen is difficult.

In order to obviate the above-mentioned drawbacks of the conventional types of liquid crystal devices, Clark and Lagerwall have proposed the use of a liquid crystal device wherein a ferroelectric liquid crystal is disposed in a thin layer having a thickness less than 5 times that of the spiral pitch thereof so that its spiral structure is unwound to develop a bistability (e.g., U.S. Pat. No. 4,367,924). As the bistable liquid crystal, a ferroelectric liquid crystal showing a chiral smectic C phase (SmC*) or H phase (SmH*) is generally used.

Such a ferroelectric liquid crystal has very rapid response speed on account of having spontaneous polarization, can also exhibit memorizable bistable state and further have excellent vision angle characteristic, and therefore it is suitable for a display of large capacity and large picture area.

Further, since a material used as a ferroelectric liquid crystal has an asymmetry, it can be used as a functional material to be used in the following types of optical devices in addition to the use as a ferroelectric liquid crystal material: (1) Those utilizing a cholesteric-nematic phase transition in a liquid crystal state (J. J. Wysoki, A. Adams and W. Haas: Phys. Rev. Lett., 20, 10204 (1968);

(2) Those utilizing a guest-host effect of the White-Taylor type in a liquid crystal state (D. L. White and G. N. Taylor: J. Appl. Phys. 45, 4718 (1974)).

These optical devices are important as display devices and modulation devices, while the explanation of the individual systems is left to the respective references and omitted.

It has been understood that, in a method utilizing an electric field-responsive optical effect of a liquid crystal, it is desirable to introduce a polar group or a group providing a polar bond in a compound constituting the liquid crystal in order to enhance the responsive characteristic of the liquid crystal. Particularly, with respect to a ferroelectric liquid crystal, it has been known that the responsive speed is proportional to its spontaneous polarization, so that it is desired to increase the spontaneous polarization in order to realize a high response speed. From this viewpoint, P. Keller et al have shown that it is possible to provide a higher response speed by introducing a chlorine atom directly connected to an asymmetric carbon atom. However, such a chlorine atom directly introduced to an asymmetric carbon atom involves problems that it is chemically unstable and lowers the stability of a liquid crystal phase as it has a large atomic radius.

On the other hand, many of optically active functional compounds for use in optical devices as described above are synthesized through an intermediate which per se is optically active. Heretofore, as optically active intermediates for synthesizing functional materials necessary for such optical devices characterized by optical activity, those compounds are known such as 2-methylbutanol, sec-octyl alcohol, sec-butyl alcohol, p-(2-methylbutyl)benzoic acid chloride, sec-phenethyl alcohol, amino acid derivatives, camphor derivatives and cholesterol derivatives. However, it has been seldom to incorporate a polar group into such an intermediate. Partly for this reason, the above mentioned method of introducing a polar group directly to an asymmetric carbon atom has not been utilized very effectively.

SUMMARY OF THE INVENTION

A principal object of the present invention is, in view of the above problems, to provide a mesomorphic compound having an enhanced electric field-responsive characteristic in an liquid crystal state by introducing a fluorine atom, which is stable and has a large dipole moment, directly to an asymmetric carbon atom.

Another object of the present invention is to provide a liquid crystal composition comprising at least one species of the mesomorphic compound.

A further object of the present invention is to provide a mesomorphic compound capable of readily changing the length of the alkyl chain and therefore capable of controlling a kind of liquid crystal phase to be developed in the liquid crystal state and a temperature range therefore as shown by H. Arnold: Z. Phys. Chem., 226, 146 (1964), and a liquid crystal composition containing at least one species of the mesomorphic compound.

According to the present invention, there is provided an optically active mesomorphic compound represented by the formula:

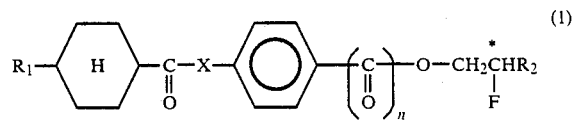 (1)

wherein $R_1$ denotes an alkyl group having 1–16 carbon atoms; $R_2$, an alkyl group having 1–18 carbon atoms; C*, an asymmetric carbon atom; X, an oxygen atom or sulfur atom; and n, 0 or 1.

According to the present invention, there is further provided a liquid crystal composition containing at least one species of the above mentioned optically active mesomorphic compound.

The present invention further provides a liquid crystal device using the liquid crystal composition.

These and other objects, features and advantages of the present invention will become more apparent upon a consideration of the following description of the preferred embodiments of the present invention.

DETAILED DESCRIPTION OF THE INVENTION

The optically active mesomorphic compound represented by the above-mentioned formula (I) of the present invention may preferably be synthesized from an optically active 2-fluoro-1-alkanol described in the specification of U.S. patent application Ser. No. 919,376 through reaction paths as shown below:

① Case where n = 0 and X is oxygen atom.

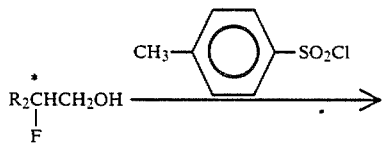

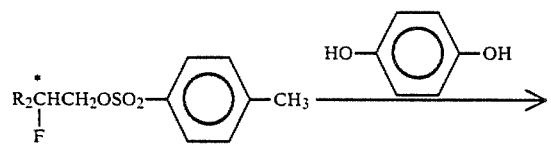

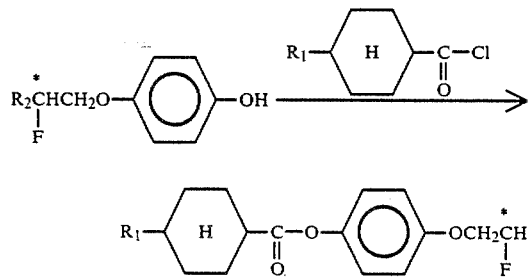

② Case wherein n = 0 and X is sulfur atom.

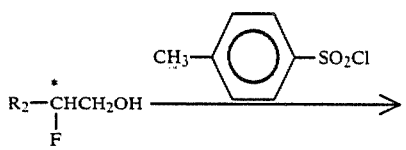

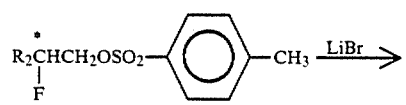

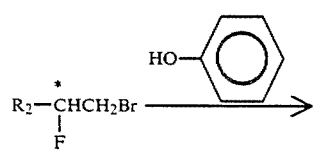

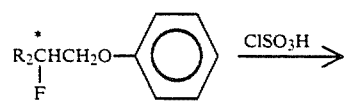

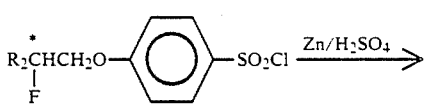

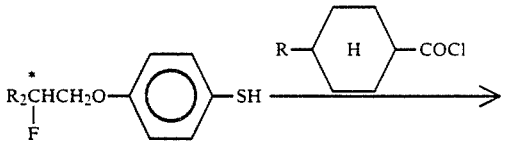

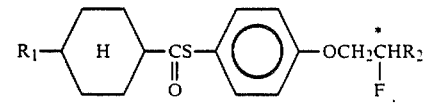

③ Case of n = 1.

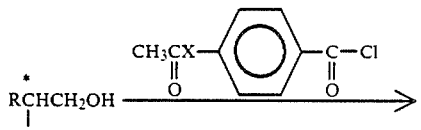

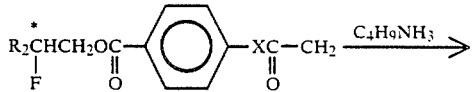

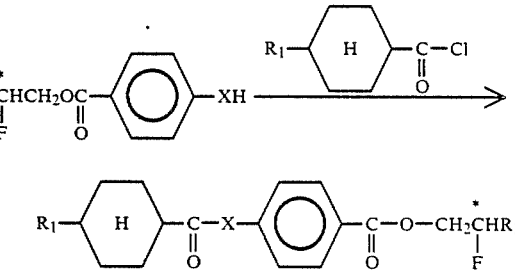

(—X— denotes —O— or —S—).

In the above cases ① – ③, $R_1$ and $R_2$ are the same as defined above.

Specific examples of the mesomorphic compound of the present invention obtained in the above-described manner are shown below.

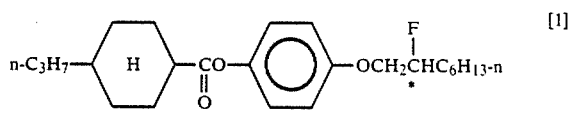
[1]

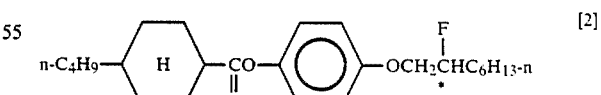
[2]

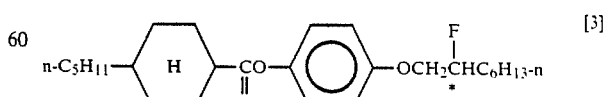
[3]

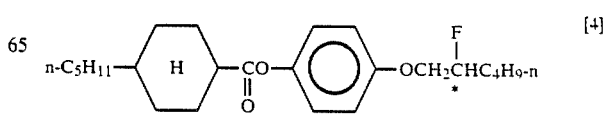
[4]

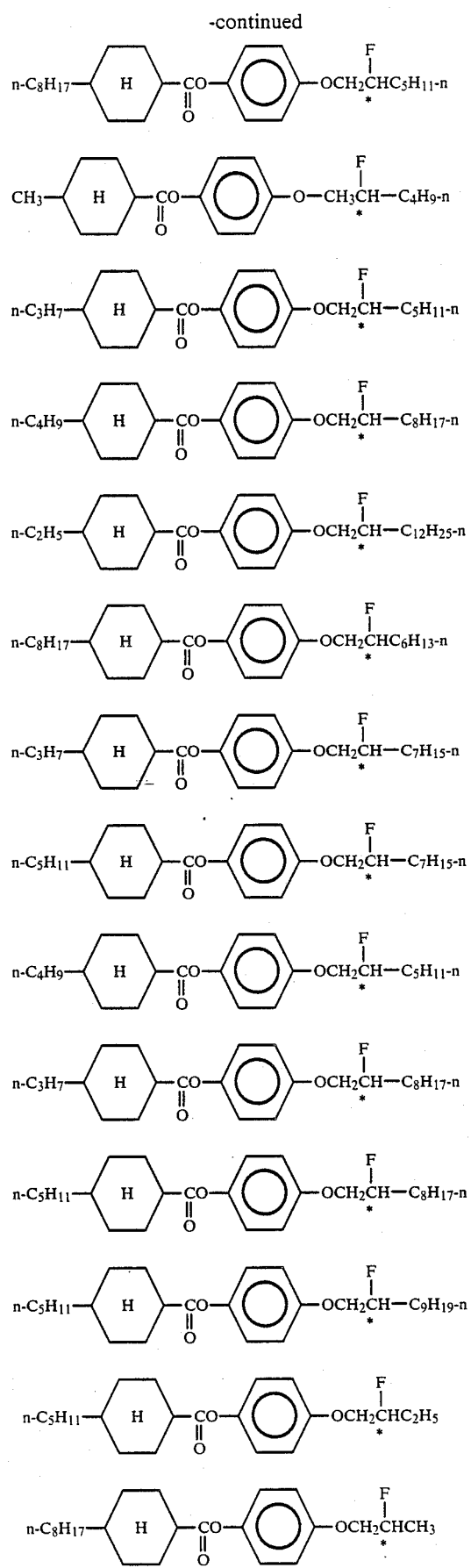
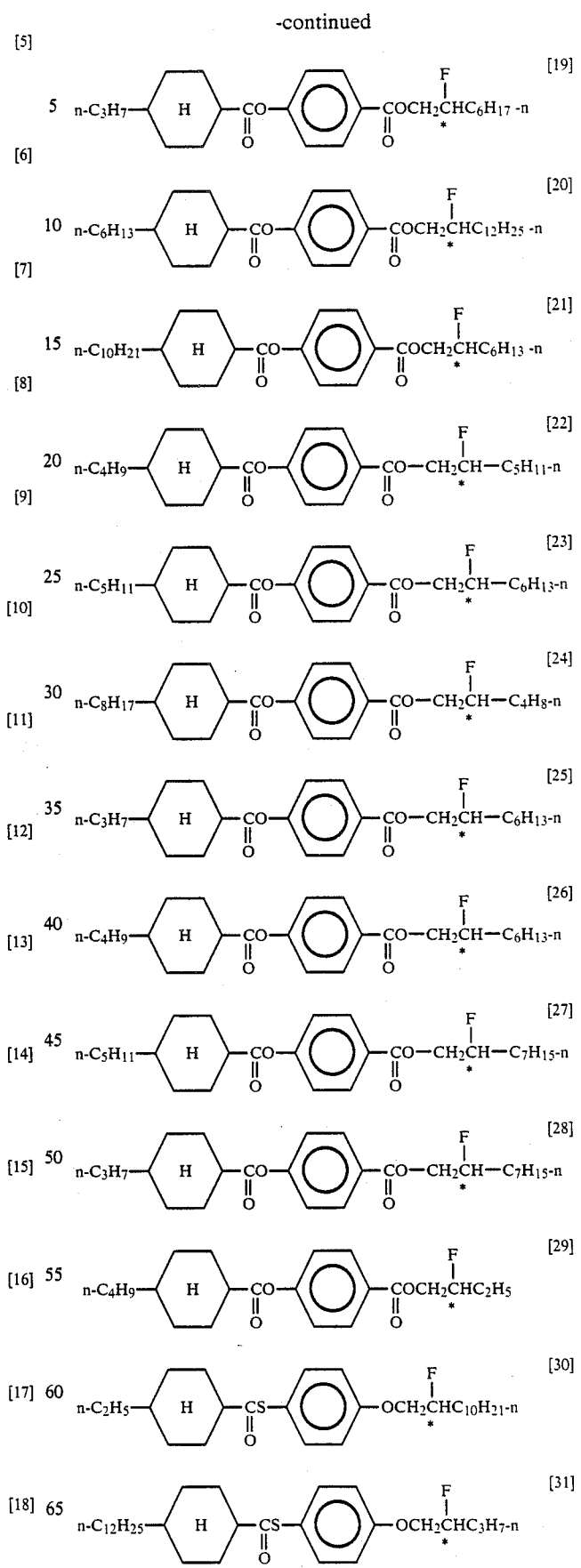

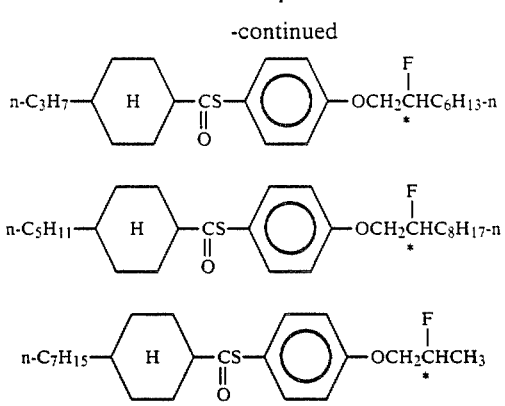

The mesomorphic compound of the present invention is characterized by having an alkylcyclohexyl groups connected to a carbonyl group in the formula (I). The mesomorphc compound of the above formula (I) having such an alkylcyclohexyl group provides a liquid crystal composition showing a faster electric field-response speed than those having an alkoxyphenyl groups or alkylphenyl group

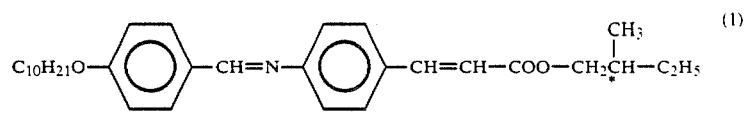

wherein $R_3$ denotes an alkyl group having 1-18 carbon atoms), when respectively added to provide such a liquid crystal composition.

The liquid crystal composition according to the present invention contains at least one species of the mesomorphic compound represented by the formula (I). For example, the mesomorphic compound represented by the formula (I) may be mixed with an optically active mesomorphic compound, preferably a ferroelectric liquid crystal compound, selected from those of the formulas (1)-(64) shown below to increase the spontaneous polarization and increase the response speed. In this case, it is preferred to use the mesomorphic compound represent by the formula (I) in an amount constituting 0.1-99 wt. %, particularly 1-90 wt. % of the resulting liquid crystal composition.

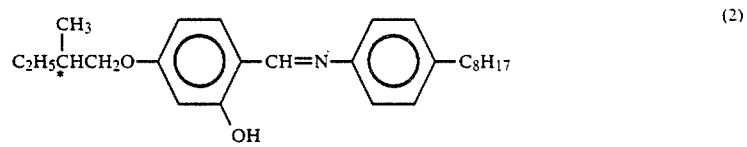

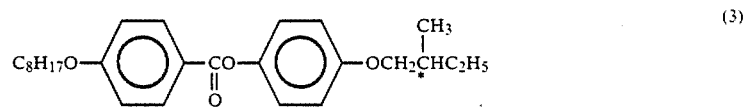

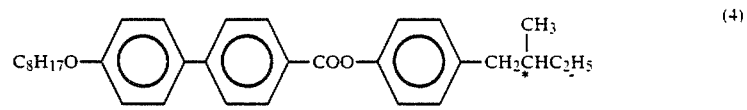

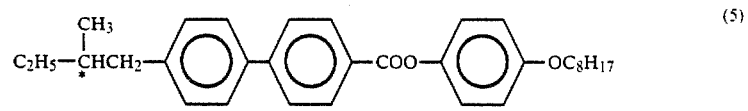

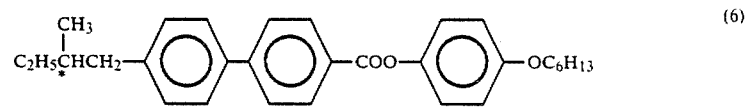

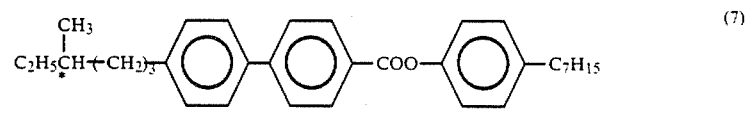

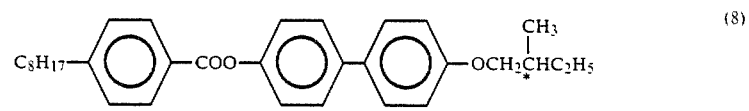

-continued
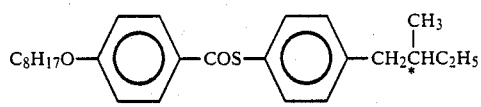
(9)
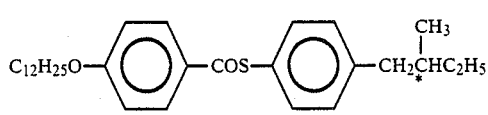
(10)
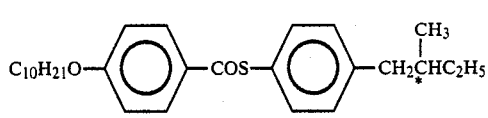
(11)
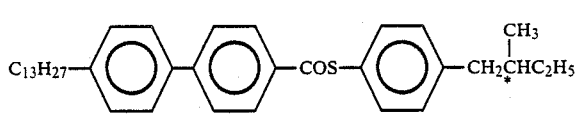
(12)
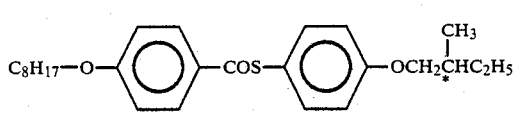
(13)
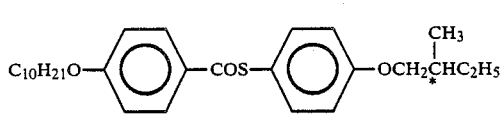
(14)
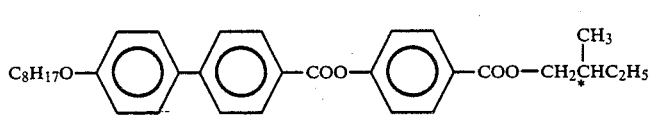
(15)
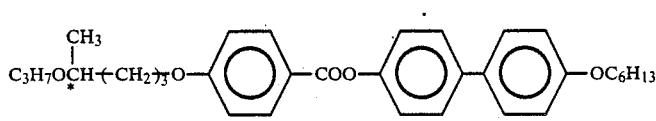
(16)
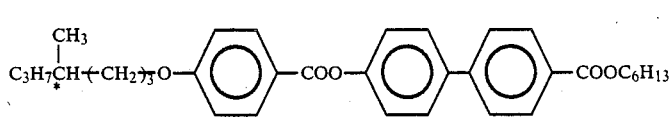
(17)
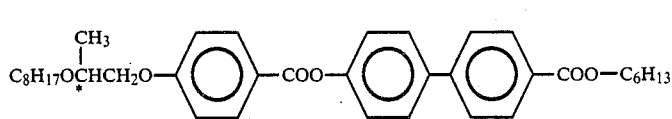
(18)
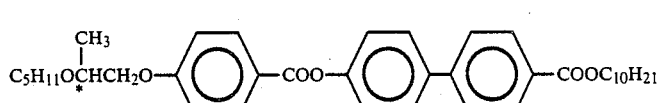
(19)
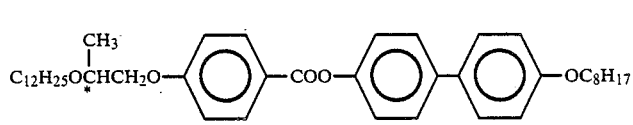
(20)
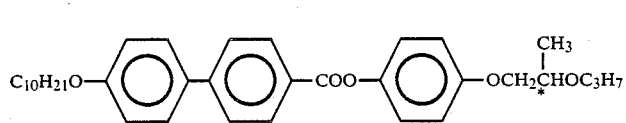
(21)
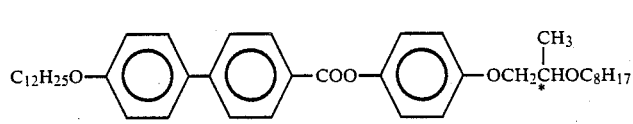
(22)

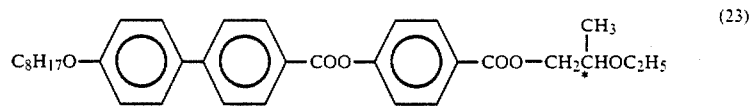
(23)
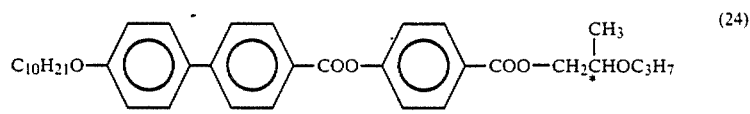
(24)
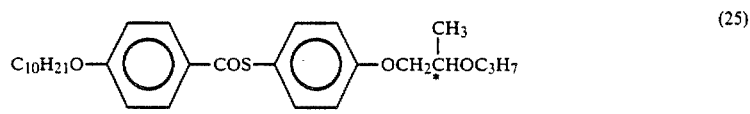
(25)
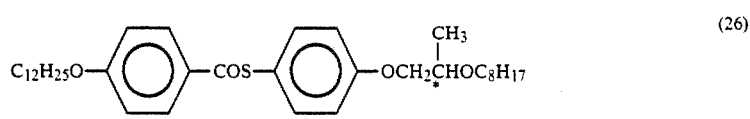
(26)
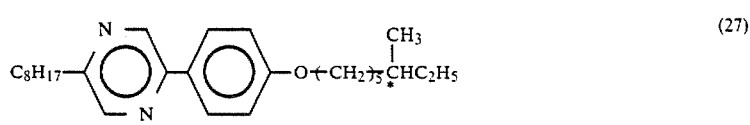
(27)
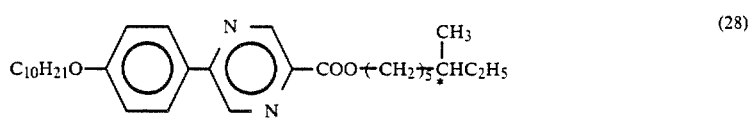
(28)
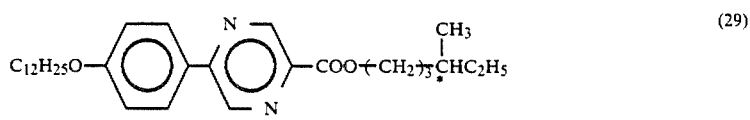
(29)
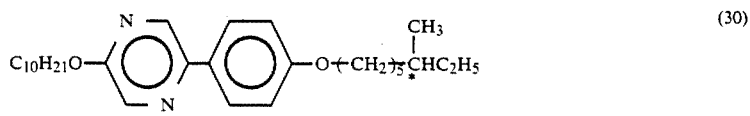
(30)
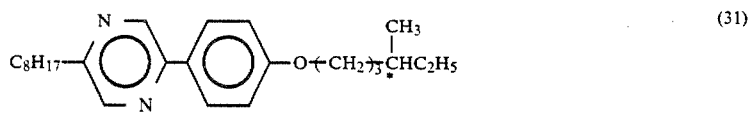
(31)
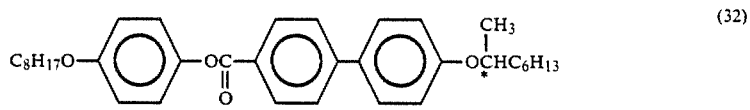
(32)
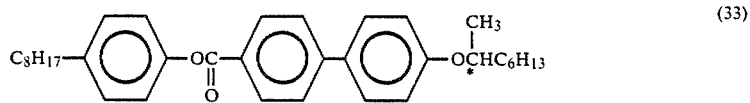
(33)
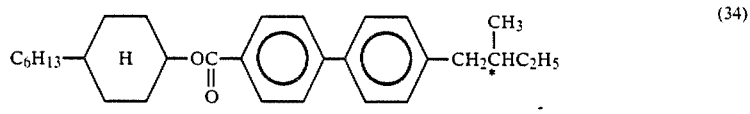
(34)
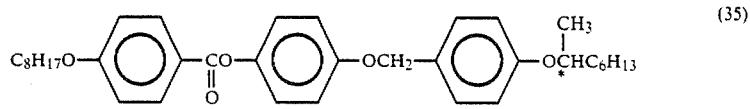
(35)

-continued

(36) $C_8H_{17}$—[pyrimidine]—OCO—[phenyl]—[phenyl]—$CH_2\overset{*}{C}H(CH_3)C_2H_5$

(37) $C_8H_{17}$—[H]—[H]—OCO—[phenyl]—O(CH$_2$)$_2$$\overset{*}{C}$H(CH$_3$)C$_2$H$_5$

(38) $C_{12}H_{25}O$—[phenyl]—[pyridine]—O(CH$_2$)$_3$$\overset{*}{C}$H(CH$_3$)C$_2$H$_5$

(39) $C_{14}H_{29}O$—[naphthyl]—COO—[phenyl]—OCH$_2$$\overset{*}{C}$H(CH$_3$)C$_2$H$_5$

(40) $C_8H_{17}$—[H]—[phenyl]—COO—[phenyl]—O(CH$_2$)$_2$$\overset{*}{C}$H(CH$_3$)OC$_5H_{11}$

(41) $C_{10}H_{21}O$—[phenyl]—CH$_2$CH$_2$—[phenyl]—OCH$_2$$\overset{*}{C}$H(CH$_3$)C$_2$H$_5$

(42) $C_{10}H_{21}O$—[phenyl]—CH$_2$CH$_2$—C(=O)—S—[phenyl]—OCH$_2$$\overset{*}{C}$H(CH$_3$)OC$_2$H$_5$

(43) $C_{10}H_{21}O$—[phenyl]—CH=CH—C(=O)O—[phenyl]—OCH$_2$$\overset{*}{C}$H(CH$_3$)OC$_2$H$_5$

(44) $C_8H_{17}O$—[phenyl]—C(=O)O—[phenyl]—CH=CH—CO—OCH$_2$$\overset{*}{C}$H(CH$_3$)OC$_2$H$_5$

(45) $C_8H_{17}O$—[phenyl]—[phenyl]—C(=O)O—[phenyl]—O$\overset{*}{C}$H(CH$_3$)—CO—C$_6$H$_{13}$

(46) $C_8H_{17}O$—[phenyl]—[phenyl]—OC(=O)—$\overset{*}{C}$H(Cl)—$\overset{*}{C}$H(CH$_3$)CHC$_2$H$_5$

(47) $C_8H_{17}$—CO—O—[phenyl]—[phenyl]—C(=O)O—CH$_2$$\overset{*}{C}$H(Cl)—CH(CH$_3$)$_2$

(48) $C_{10}H_{21}O$—[phenyl]—[phenyl]—C(=O)O—[phenyl]—OCH$_2$$\overset{*}{C}$H(F)C$_8$H$_{17}$ -continued
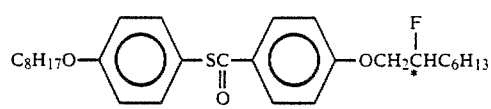 (49)
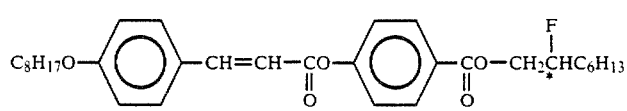 (50)
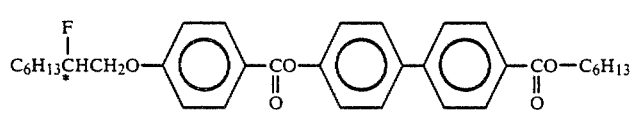 (51)
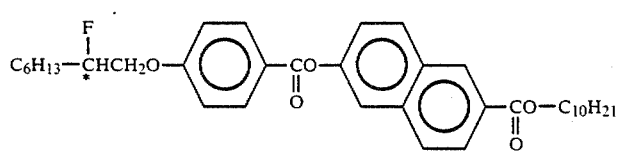 (52)
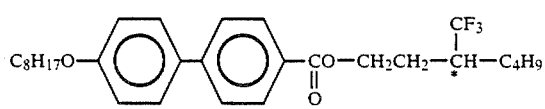 (53)
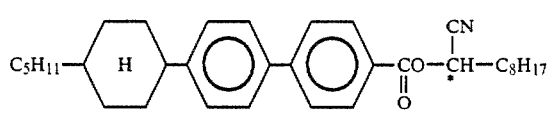 (54)
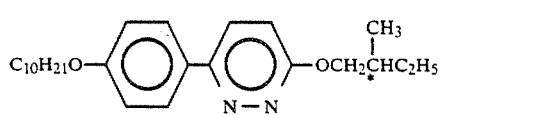 (55)
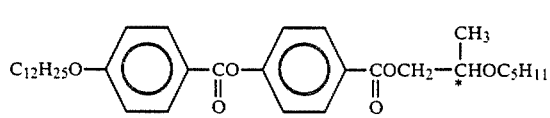 (56)
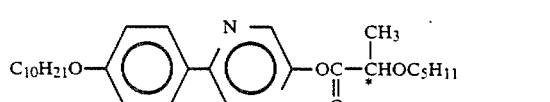 (57)
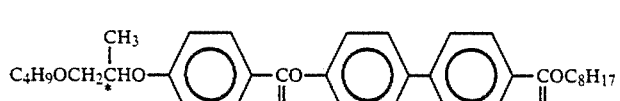 (58)
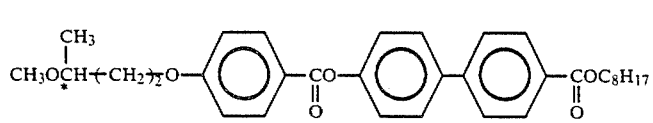 (59)
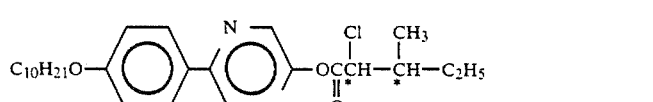 (60)
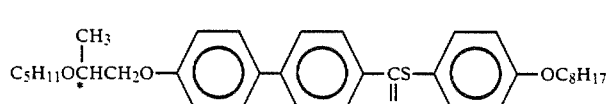 (61)

-continued

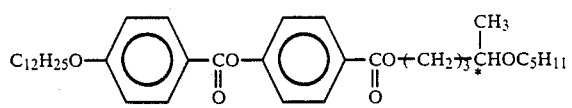
(62)

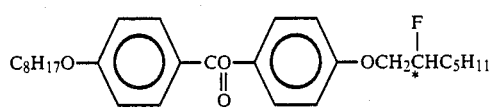
(63)

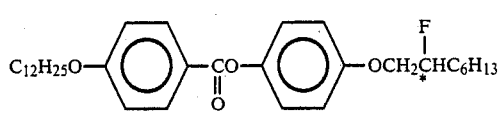
(64)

The mesomorphic compound represented by the formula (I) may also be mixed with a mesomorphic compound such as those of the formulas [1]–[17] shown below which per se are not chiral to provide a composition which may be used as a ferroelectric liquid crystal. In this case, the mesomorphic compound represented by the formula (I) may preferably be used in an amount of 0.1–99 wt. %, particularly 1–90 wt. %. The resultant composition may be provided with an increased spontaneous polarization corresponding to the content of a mesomorphic compound according to the present invention.

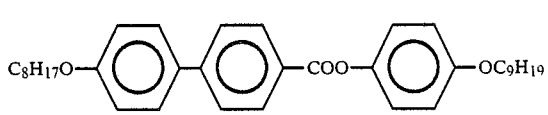
(1)

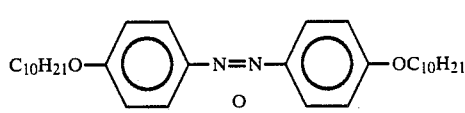
(2)

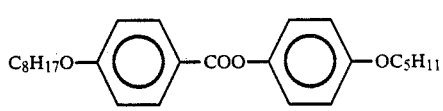
(3)

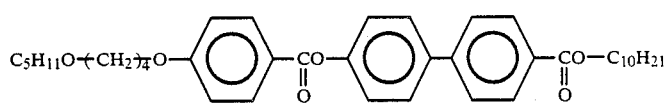
(4)

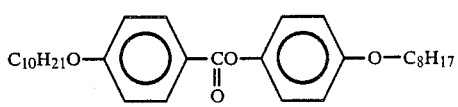
(5)

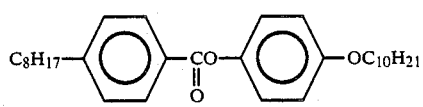
(6)

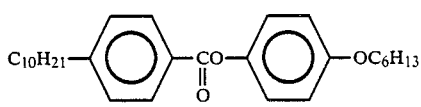
(7)

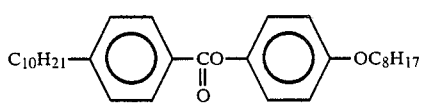
(8)

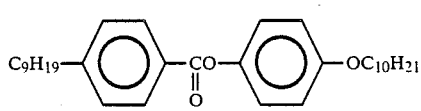
(9)

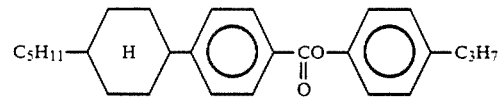 (10)

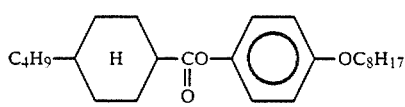 (11)

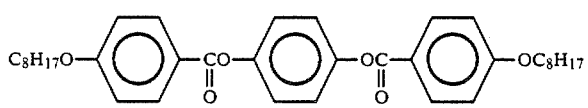 (12)

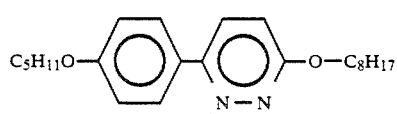 (13)

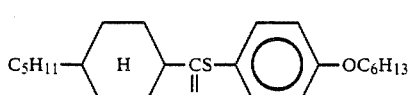 (14)

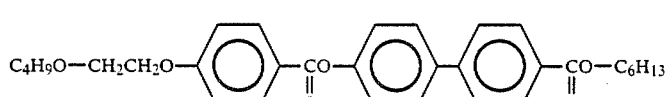 (15)

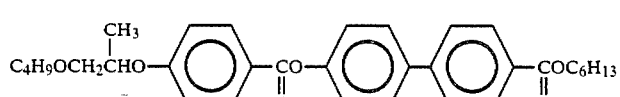 (16)

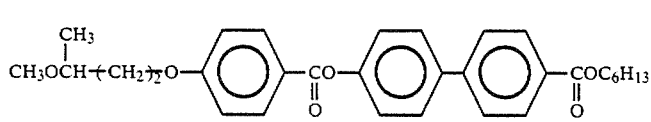 (17)

Hereinbelow, the present invention will be explained more specifically with reference to some examples.

EXAMPLE 1

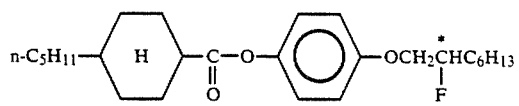

Trans-4-n-pentylcyclohexane-carboxylic acid-p-2-fluorooctyloxyphenyl-ester represented by the above formula was prepared along the following reaction scheme:

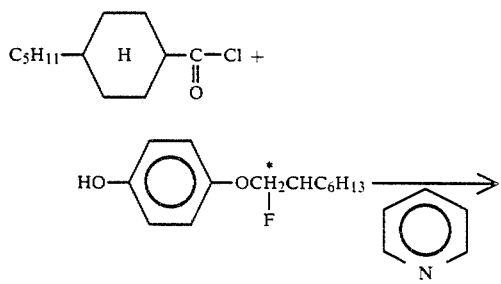

-continued

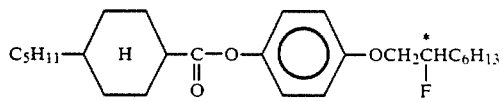

1.00 g (4.16 mM) of p-2-fluorooctyloxyphenol was dissolved in 10 ml of pyridine and 5 ml of toluene, and then a solution of 1.30 g (6.00 mM) of trans-4-n-pentyl-cyclohexane-carboxylic acid chloride in 5 ml of toluene was added thereto dropwise below 5° C. in 20–40 minutes. After the addition, the mixture was stirred overnight at room temperature to obtain a white precipitate.

After the reaction the product was extracted with benzene, and the resultant benzene layer was washed with water and dried on magnesium sulfate, followed by removal of benzene by distillation. The product was further purified by silica gel column chromatography and recrystallized from ethanol/methanol to obtain 1.20 g (2.85 mM) of trans-4-n-pentylcyclohexane-carboxylic acid-p-2-fluorooctyloxyphenyl ester (Yield: 68.6%).

NMR date (ppm): 0.83–2.83 ppm (34H, m), 4.00–4.50 ppm (2H, q), 7.11 ppm (4H, s)

IR data (cm$^{-1}$): 3456, 2928, 2852, 1742, 1508, 1470, 1248, 1200, 1166, 1132, 854.

Phase transition temperature (°C.):

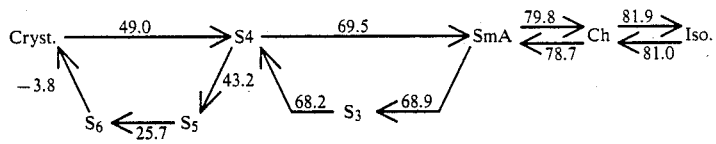

Herein, the symbols respectively denote the following phases:
Cryst: crystal phase,
SmA: smectic A phase,
Ch: cholesteric phase, Iso: isotropic phase,
SmC*: chiral smectic phase,
$S_3$, $S_4$, $S_5$, $S_6$ phase showing a higher degree of order than SmC*.

EXAMPLE 2

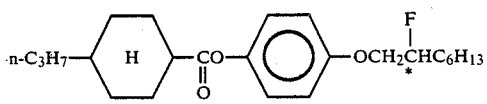

Trans-4-n-propylcyclohexane-carboxylic acid-p-2-fluorooctyloxyphenyl ester of the above formula was synthesized along a similar reaction scheme as in Example 1.

More specifically, 0.60 g (2.50 mM) of 2-fluorooctyloxyphenol was dissolved in 10 ml of pyridine and 5 ml of toluene, and then a solution of 0.61 g (3.25 mM) of trans-4-n-propylcyclohexane-carboxylic acid chloride in 5 ml of toluene was added thereto dropwise below 5° C. in 20–40 minutes. Thereafter, according to a similar procedure as in Example 1, 0.88 g (2.24 mM) of trans-4-n-propylcyclohexane-carboxylic acid-p-2-fluorooctyloxyphenyl ester (Yield: 89.6%).

Phase transition temperatures (°C.)

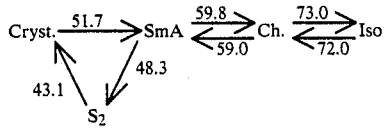

EXAMPLE 3

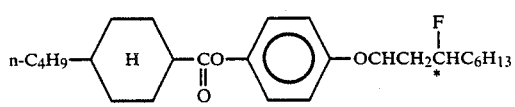

Trans-4-n-butylcyclohexane-carboxylic acid-p-2-fluorooctyloxyphenyl ester of the above formula was synthesized along a similar reaction scheme as in Example 1.

More specifically, 0.60 g (2.50 mM) of 2-fluorooctyloxyphenol was dissolved in 10 ml of pyridine and 5 ml of toluene, and then a solution of 0.66 g (3.25 mM) of trans-4-n-butylcyclohexane-carboxylic acid chloride in 5 ml of toluene was added thereto dropwise below 5° C. in 20–40 minutes. Thereafter, according to a similar procedure as in Example 1, 0.83 g (2.04 mM) of trans-4-n-butylcyclohexane-carboxylic acid-p-2-fluorooctyloxyphenyl ester (Yield: 81.6%).

Phase transition temperature (°C.)

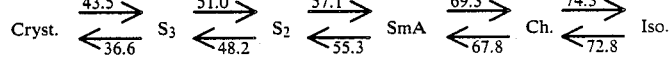

EXAMPLE 4

(1) Synthesis of trans-4-n-octylcyclohexane-carboxylic acid chloride.

1.16 g (4.82 mM) of trans-4-n-octylcyclohexane-carboxylic acid was added to thionyl chloride, and the mixture was heated at 60° C. for 3 hours, followed by distilling-off of an excess of the thionyl chloride, to obtain 1.00 g (3.86 mM) of trans-4-n-octylcyclohexane-carboxylic acid chloride.

(2)

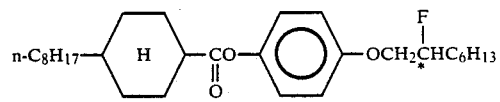

Trans-4-n-octylcyclohexane-carboxylic acid-p-2-fluorocotylphenyl ester of the above formula was synthesized along a similar reaction scheme as in Example 1.

More specifically, 0.60 g (2.50 mM) of 2-fluorooctyloxyphenol was dissolved in 10 ml of pyridine and 5 ml of toluene, and then a solution of 0.84 g (3.24 mM) of trans-4-n-octylcyclohexane-carboxylic acid chloride in 5 ml of toluene was added thereto dropwise below 5° C. in 20–40 minutes. Thereafter, according to a similar procedure as in Example 1, 0.88 g (1.90 mM) of trans-4-n-octylcyclohexane-carboxylic acid-p-2-fluorooctyloxyphenyl ester (Esterification Yield: 76.0%).

Phase transition temperatures (°C.)

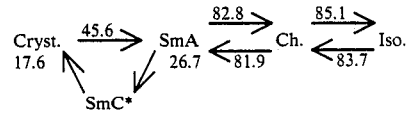

EXAMPLE 5

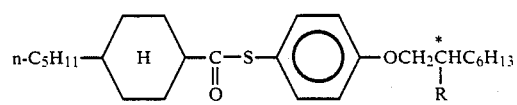

Trans-4-n-pentylcyclohexanethiocarboxyl acid-s-p-2-fluorodecyloxyphenyl-ester was prepared along the following reaction scheme:

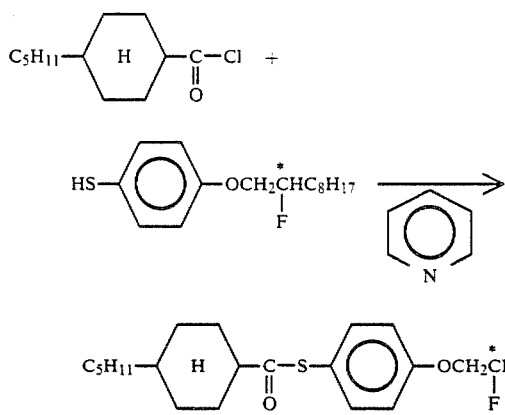

1.00 g (3.52 mM) of 2-fluorodecyloxybenzenethiol was dissolved in 10 ml of pyridine and 5 ml of toluene, and a solution of 1.00 g (4.62 mM) of trans-4-n-pentylcyclohexane-carboxylic acid chloride in 5 ml of toluene was added dropwise thereto in a nitrogen atmosphere below 5° C. in 20-40 minutes. After the addition, the mixture was further stirred for several hours at room temperature to obtain a white precipitate.

After the reaction, the product was extracted with benzene, and the resultant organic layer was washed with distilled water and dried on magnesium sulfate, followed by distilling-off of benzene and purification by reverse phase silica gel column chromatography to obtain 0.58 g (1.25 mM) of trans-4-n-pentylcyclohexane-thiocarboxylic acid-s-p-2-fluorodecyloxyphenyl ester (Yield: 36%).

NMR date (ppm): 0.67-2.33 ppm (38H, m), 3.83-4.67 ppm (2H, q), 6.83-7.50 ppm (4H, q)

IR data (cm$^{-1}$): 3460, 2920, 2852, 1696, 1596, 1498, 1292, 1250, 944, 838, 806.

Phase transition temperature (°C.):

$$\text{Cryst.} \underset{70.7}{\overset{81.2}{\rightleftarrows}} \text{Iso.}$$

EXAMPLE 6

The following liquid crystal composition A containing the mesomorphic compound prepared in Example 1 was prepared. For comparison, the following liquid crystal composition B not containing the mesomorphic compound of Example 1 was prepared. The phase transition temperatures and spontaneous polarization data of the liquid crystal compositions A and B, respectively, are shown below.

<L.C. composition>

(3) n-C$_8$H$_{17}$O—⬡—COO—⬡—OCH$_2$C*HC$_2$H$_5$ / CH$_3$    56 wt. %

(5) n-C$_8$H$_{17}$O—⬡—OCO—⬡—CH$_2$C*HC$_2$H$_5$ / CH$_3$    14 wt. %

[3] n-C$_5$H$_{11}$—H—COO—⬡—OCH$_2$C*HC$_6$H$_{13}$ / F    30 wt. %

Phase transition temperature (°C.)

$$\text{Cryst.} \underset{4}{\overset{11}{\rightleftarrows}} \text{SmC*} \underset{42}{\overset{43}{\rightleftarrows}} \text{SmA} \underset{68}{\overset{69}{\rightleftarrows}} \text{Ch.} \underset{75}{\overset{76}{\rightleftarrows}} \text{Iso.}$$

<L.C. Composition B>

(3) n-C$_8$H$_{17}$O—⬡—COO—⬡—OCH$_2$C*HC$_2$H$_5$ / CH$_3$    80 wt. %

(5) n-C$_8$H$_{17}$O—⬡—OCO—⬡—⬡—CH$_2$C*HC$_2$H$_5$ / CH$_3$    20 wt. %

Phase transition temperature (°C.)

$$\text{Cryst.} \underset{18}{\overset{20}{\rightleftarrows}} \text{SmC*} \underset{52}{\overset{53}{\rightleftarrows}} \text{SmA} \underset{64}{\overset{65}{\rightleftarrows}} \text{Ch.} \underset{75}{\overset{76}{\rightleftarrows}} \text{Iso.}$$

Spontaneous polarization (nC/cm$^2$)

| Temp. (°C.) | L. C. Composition A | L. C. Composition B |
|---|---|---|
| 30 | 8.6 | 2.0 |

Then, two 0.7 mm-thick glass plates were provided and respectively coated with an ITO film to form an electrode for voltage application, which was further coated with an insulating layer of vapor-deposited $SiO_2$. On the insulating layer, a 0.2%-solution of silane coupling agent (KBM-602, available from Shinetsu Kagaku K.K.) in isopropyl alcohol was applied by spinner coating at a speed of 2000 rpm for 15 second and subjected to hot curing treatment at 120° C. for 20 min.

Further, each glass plate provided with an ITO film and treated in the above described manner was coated with a 1.5%-solution of polyamide resin precursor (SP-510, available from Toray K.K.) in dimethylacetoamide by a spinner coater rotating at 2000 rpm for 15 seconds. Thereafter, the coating film was subjected to heat curing at 300° C. for 60 min. to obtain about 250 A-thick film. the coating film was rubbed with acetate fiber-planted clot. The thus treated two glass plates were washed with isopropyl alcohol. After alumina beads with an average particle size of 2 microns were dispersed on one of the glass plates, the two glass plates were applied to each other with a bonding sealing agent (Lixon Bond available from Chisso K.K) so that their rubbed directions were parallel to each other and heated at 100° C. for 60 min. to form a blank cell. The cell gap was found to be about 2 microns as measured by a Berek compensator.

Two blank cells were prepared in the above-described manner and filled under vacuum with the above-prepared ferroelectric liquid crystal compositions A and B, respectively, heated into a uniform isotropic liquid mixture, followed by gradual cooling at a rate of 0.5° C./hour, to prepare two ferroelectric liquid crystal devices.

The ferroelectric liquid crystal devices were subjected to measurement of an optical response time (time from voltage application until the transmittance change reaches 90% of the maximum under the application of a peak-to-peak voltage Vpp of 30 V in combination with right-angle cross-nicol polarizers). The results are shown below:

| Temp °C. | L. C. Comp. A | L. C. Comp. B |
|---|---|---|
| 30 | 12 μsec | 930 μsec |

The above results show that the liquid crystal composition A obtained by mixing the liquid crystal composition B and trans-4-n-pentylcyclohexanecarboxylic acid in a ratio of 7:3, showed a markedly improved response speed compared with the liquid crystal composition B alone.

EXAMPLE 7

The following liquid crystal composition C containing the mesomorphic compound prepared in Example 1 was prepared. For comparison, the following liquid crystal composition D not containing the mesomorphic compound of Example 1 was prepared. The phase transition temperatures and spontaneous polarization data of the liquid crystal compositions C and D, respectively, are shown below.

<L.C. Composition C>

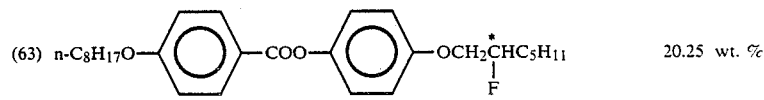

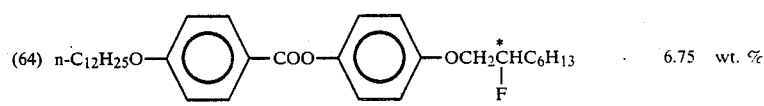

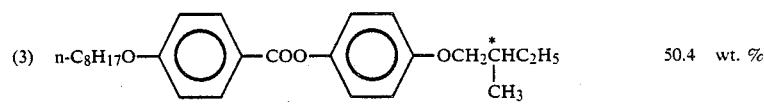

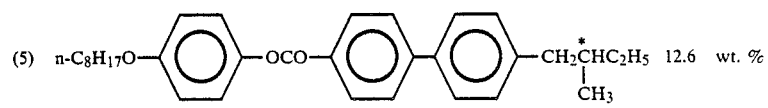

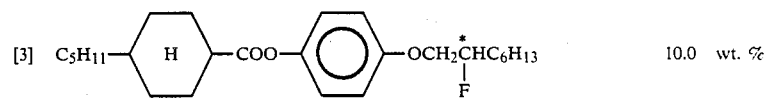

Phase transition temperature (°C.)

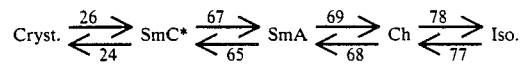

<L.C Composition D>

(63) 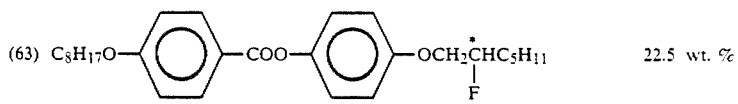 22.5 wt. %

(64) 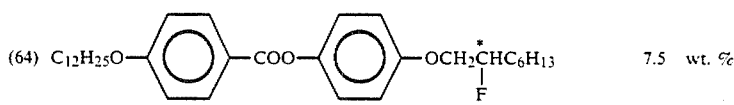 7.5 wt. %

(3) 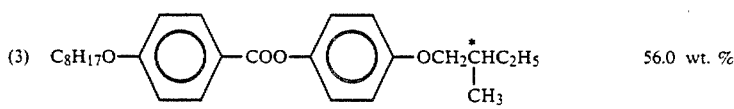 56.0 wt. %

(5) 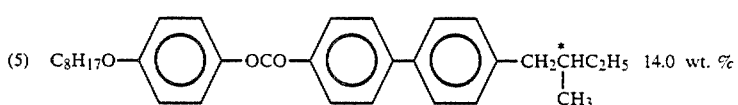 14.0 wt. %

Phase transition temperature (°C.)

$$\text{Cryst.} \underset{22}{\overset{24}{\rightleftarrows}} \text{SmC*} \underset{48}{\overset{49}{\rightleftarrows}} \text{SmA} \underset{68}{\overset{69}{\rightleftarrows}} \text{Ch.} \underset{78}{\overset{78}{\rightleftarrows}} \text{Iso.}$$

Spontaneous polarization (nC/cm²)

| Temp. (°C.) | L. C. Comp. C | L. C. Comp. D |
|---|---|---|
| 30 | 29.3 | 32.8 |
| 25 | 36.7 | 36.5 |

The ferroelectric liquid crystal compositions C and D were respectively heated into a uniform isotropic liquid mixture and charged into two blank cells prepared in the same manner as in Example 6, followed by cooling from the isotropic phase at a rate of 0.5° C./hour, to prepare two ferroelectric liquid crystal devices. These devices were subjected to measurement of an optical response time in the same manner as in Example 6. The results are shown below.

Response time (μsec)

| Temp. (°C.) | L. C. Comp. C | L. C. Comp. D |
|---|---|---|
| 30 | 28.1 | 59.8 |
| 25 | 53.6 | 106.3 |

The above results show that liquid crystal composition C obtained by mixing the liquid crystal composition D and trans-4-n-pentylcyclohexanecarboxylic acid-p-2-fluorooctyloxyphenyl ester in a ratio of 9:1, showed an improved response speed compared with the liquid crystal composition D.

Further, the comparison between the liquid crystal composition A of Example 1 and the liquid crystal composition D respectively containing a fluoroalkyl ester mesomorphic compound, the liquid crystal composition A containing a mesomorphic compounds having an alkylcyclohexyl group represented by the formula (I) showed a better response characteristic than the liquid crystal composition D containing a mesomorphic compound having an alkoxyphenyl group instead of the alkylcyclohexyl group.

EXAMPLE 8

A liquid crystal composition E was prepared by mixing the following example mesomorphic compounds in the respectively indicated proportions.

| Ex. Comp. No. | Structural formula | wt. parts |
|---|---|---|
| (8) | 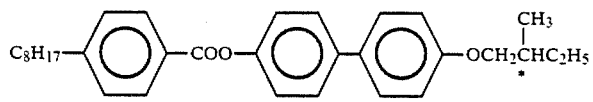 | 15 |
| (16) | 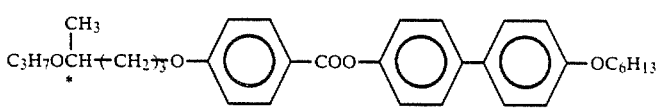 | 5 |
| (17) | 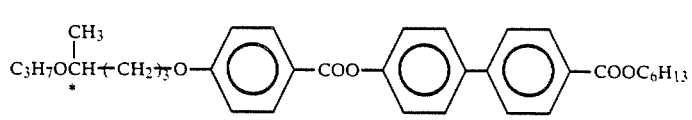 | 10 |

-continued

| Ex. Comp. No. | Structural formula | wt. parts |
|---|---|---|
| (5) | $C_{10}H_{21}O$-⟨⟩-COO-⟨⟩-$OC_8H_{17}$ | 5 |
| (6) | $C_8H_{17}$-⟨⟩-COO-⟨⟩-$OC_{10}H_{21}$ | 8 |
| (7) | $C_{10}H_{21}O$-⟨⟩-COO-⟨⟩-$OC_6H_{13}$ | 5 |
| (8) | $C_{10}H_{21}$-⟨⟩-COO-⟨⟩-$OC_8H_{17}$ | 12 |
| (13) | $C_8H_{17}O$-⟨⟩-COS-⟨⟩-$OCH_2\overset{*}{C}H(CH_3)C_2H_5$ | 9 |
| (14) | $C_{10}H_{21}O$-⟨⟩-COS-⟨⟩-$OCH_2\overset{*}{C}H(CH_3)C_2H_5$ | 6 |
| (58) | $C_4H_9OCH_2\overset{*}{C}H(CH_3)O$-⟨⟩-COO-⟨⟩-⟨⟩-$COOC_8H_{17}$ | 5 |
| (56) | $C_{12}H_{25}O$-⟨⟩-COO-⟨⟩-$COOCH_2\overset{*}{C}H(CH_3)OC_5H_{11}$ | 15 |
| (62) | $C_{12}H_{25}O$-⟨⟩-COO-⟨⟩-$COO$$\text{-}(CH_2)_3\overset{*}{C}H(CH_3)OC_5H_{11}$ | 5 |

Then, a liquid crystal composition F was prepared by mixing the liquid crystal composition E with Example compound [24] according to the formula (I) of the present invention in a ratio of 94:6.

Then, two liquid crystal devices were prepared by using the compositions E and F in the same manner as in Example 6 except that the cell gap (liquid crystal layer thickness) was reduced to 1.5 micron and were subjected to measurement of an optical response time in the same manner as in Example 6 except that the peak-to-peak voltage was charged to 25 V. The results are shown below:

Response time (μsec)

|  | 40° C. | 25° C. | 10° C. |
|---|---|---|---|
| L. C. Comp. E | 155 | 435 | 1410 |
| L. C. Comp. F | 105 | 290 | 850 |

The above results show that the inclusion of a mesomorphic compound of the present invention into the liquid crystal composition E caused an improvement in response characteristic.

EXAMPLE 9

A liquid crystal composition G was prepared by mixing the liquid crystal composition E used in Example 8 with Example compounds 22 and 29 represented by the general formula (I) of the present invention in ratios of 95:3:2. Then, a liquid crystal device was prepared by using the liquid crystal composition otherwise in the same manner as in Example 8 and subjected to measurement of the optical response time in quite the same manner as in Example 8. The results are shown below together with those obtained by using the composition E:

Response time (μsec)

|  | 40° C. | 25° C. | 10° C. |
|---|---|---|---|
| L. C. Comp. E | 155 | 435 | 1410 |

| | 40° C. | 25° C. | 10° C. |
|---|---|---|---|
| -continued | | | |
| L. C. Comp. G | 100 | 305 | 880 |

The above results again show that the inclusion of a mesomorphic compound of the present invention into the liquid crystal composition E caused an improvement in response characteristics.

EXAMPLE 10

A liquid crystal composition H was prepared by mixing the following example mesomorphic compounds in the respectively indicated proportions:

| Ex. Comp. No. | Structural formula | wt. parts |
|---|---|---|
| (5) | $C_{10}H_{21}O$—⌬—COO—⌬—$OC_8H_{17}$ | 6 |
| (6) | $C_8H_{17}$—⌬—COO—⌬—$OC_{10}H_{21}$ | 8 |
| (7) | $C_{10}H_{21}O$—⌬—COO—⌬—$OC_6H_{13}$ | 9 |
| (8) | $C_{10}H_{21}$—⌬—COO—⌬—$OC_8H_{17}$ | 12 |
| (9) | $C_8H_{17}O$—⌬—COS—⌬—$CH_2\overset{*}{C}H(CH_3)C_2H_5$ | 3 |
| (10) | $C_{12}H_{25}O$—⌬—COS—⌬—$CH_2\overset{*}{C}H(CH_3)C_2H_5$ | 3 |
| (13) | $C_8H_{17}O$—⌬—COS—⌬—$OCH_2\overset{*}{C}H(CH_3)C_2H_5$ | 3 |
| (14) | $C_{10}H_{21}O$—⌬—COS—⌬—$OCH_2\overset{*}{C}H(CH_3)C_2H_5$ | 3 |
| (17) | $C_3H_7O\overset{*}{C}H(CH_3)(CH_2)_3O$—⌬—COO—⌬—⌬—$COOC_6H_{13}$ | 15 |
| (58) | $C_4H_9OCH_2\overset{*}{C}H(CH_3)O$—⌬—COO—⌬—⌬—$COOC_8H_{17}$ | 15 |
| (59) | $CH_3O\overset{*}{C}H(CH_3)(CH_2)_2O$—⌬—COO—⌬—⌬—$COOC_8H_{17}$ | 8 |
| (56) | $C_{12}H_{25}O$—⌬—COO—⌬—COO—$CH_2\overset{*}{C}H(CH_3)OC_5H_{11}$ | 9 |

| Ex. Comp. No. | Structural formula | wt. parts |
|---|---|---|
| (62) | 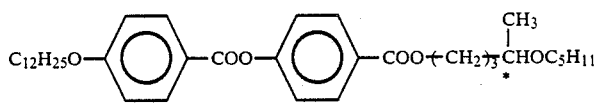 | 6 |

Then, a liquid crystal composition I was prepared by mixing the above liquid crystal composition H with Example compounds [22] and [29] represented by the general formula (I) of the present invention in ratios of 93:3:4. Then, liquid crystal devices were prepared by using the liquid crystal compositions H and I otherwise in the same manner as in Example 8 and subjected to measurement of the optical response time in quite the same manner as in Example 8. The results are shown below:

Response time (μsec)

|  | 40° C. | 25° C. | 10° C. |
|---|---|---|---|
| L. C. Comp. H | 137 | 374 | 1260 |
| L. C. Comp. I | 106 | 277 | 802 |

EXAMPLE 11

An liquid crystal device was prepared in the same manner as in Example 6 except that a liquid crystal CS 1011 (available from Chisso K.K.; having a negative dielectric of $\Delta\epsilon \simeq -3.9$ (sine wave, 100 kHz)) was used and disposed in a cell gap of 1.5 micron.

The above liquid crystal device showed a tilt angle of 6.8 degrees when measured under right angle cross nicols at 25° C. Then, when the liquid crystal device was observed through a polarizing microscope while being supplied with AC rectangular waves of ±8 V and a frequency of 60 kHz, the liquid crystal device showed a tilt angle of 13 degrees and an increased contrast ratio of 35:1. This means that the display characteristics of the liquid crystal CS 1011 was improved as a result of the AC stabilization effect. Then, the liquid crystal device was subjected to the measurement of an optical response time in the same manner as in Example 8. The results are shown below:

Response time (μsec)

| 40° C. | 25° C. | 10° C. |
|---|---|---|
| 120 | 670 | 2090 |

Then, the liquid crystal CS 1011 was mixed with Example compound [11] as an example of the mesomorphic compound represented by the general formula (I) of the present invention in a ratio of 9:1 to obtain a liquid crystal composition J.

A liquid crystal device was prepared by using the liquid crystal composition J in the same manner as in the case of the liquid crystal CS 1011 alone and subjected to measurement of tilt angle whereby the following results were obtained.

|  | Tilt Angle | |
|---|---|---|
| As prepared | Under rectangular AC application of 60 kHz 80 V | |
| 7.2 degrees | 13.3 degrees | |

Then, the optical response time (μsec) was measured in the same manner as above the results are show below:

Response time (μsec)

|  | 40° C. | 25° C. | 15° C. |
|---|---|---|---|
| L. C. Comp. J | 80 | 450 | 1200 |

The above results show that the mixing of a mesomorphic compound according to the present invention with the liquid crystal CS 1011 provided a liquid crystal composition and device retaining the AC stabilization effect of the liquid crystal CS 1011 and further showing improved response characteristics.

What is claimed is:

1. An optically active mesomorphic compound represented by the formula:

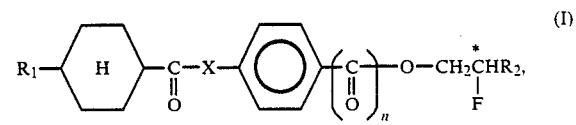 (I)

wherein $R_1$ denotes an alkyl group having 1–16 carbon atoms; $R_2$ denotes an alkyl group having 1–18 carbon atoms; C* is an asymmetric carbon atom; X is an oxygen atom or sulfur atom; and n is 0 or 1.

2. A compound according to claim 1, which is

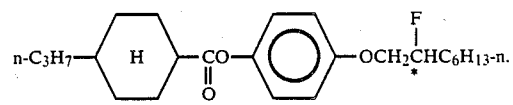

3. A compound according to claim 1, which is

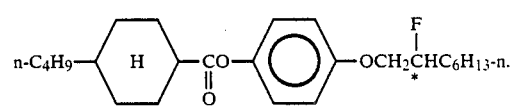

4. A compound according to claim 1, which is

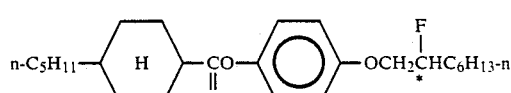

5. A compound according to claim 1, which is

6. A compound according to claim 1, which is

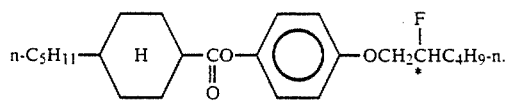

7. A compound according to claim 1, which is

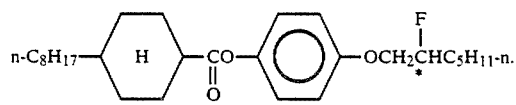

8. A compound according to claim 1, which is

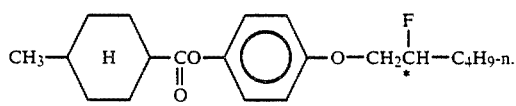

9. A compound according to claim 1, which is

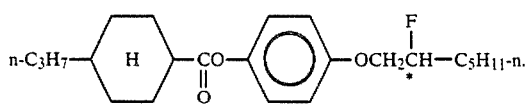

10. A compound according to claim 1, which is

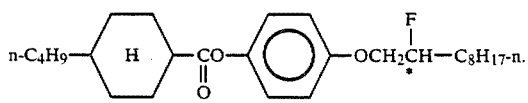

11. A compound according to claim 1, which is

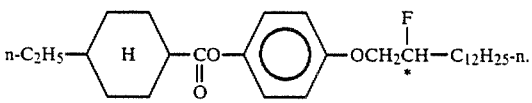

12. A compound according to claim 1, which is

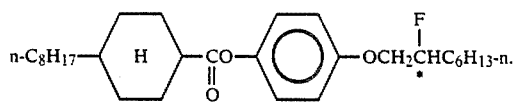

13. A compound according to claim 1, which is

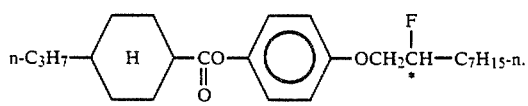

14. A compound according to claim 1, which is

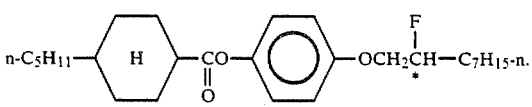

15. A compound according to claim 1, which is

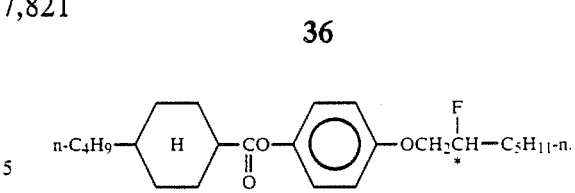

16. A compound according to claim 1, which is

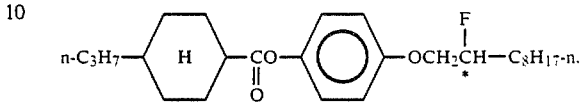

17. A compound according to claim 1, which is

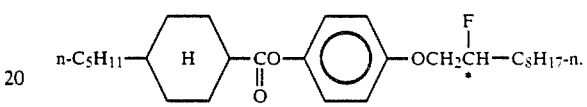

18. A compound according to claim 1, which is

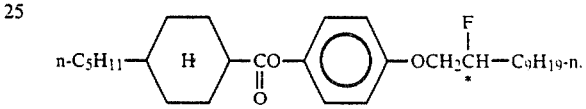

19. A compound according to claim 1, which is

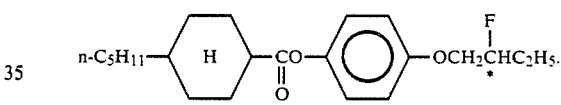

20. A compound according to claim 1, which is

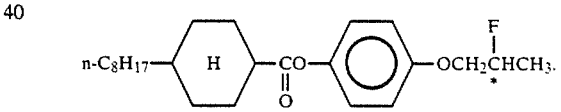

21. A compound according to claim 1, which is

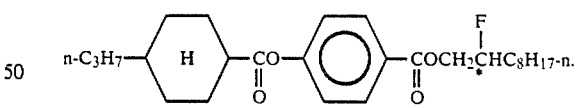

22. A compound according to claim 1, which is

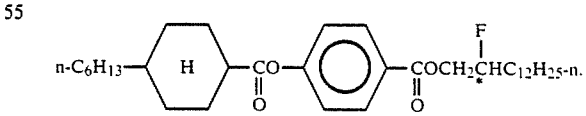

23. A compound according to claim 1, which is

24. A compound according to claim 1, which is

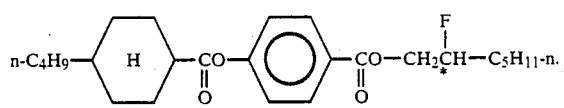

25. A compound according to claim 1, which is

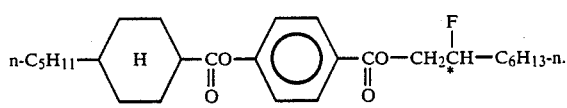

26. A compound according to claim 1, which is

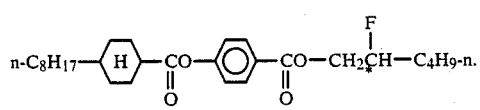

27. A compound according to claim 1, which is

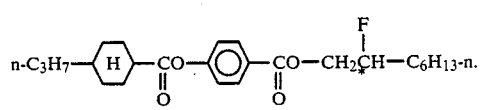

28. A compound according to claim 1, which is

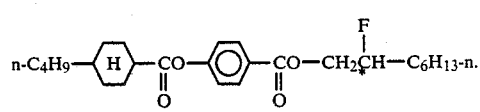

29. A compound according to claim 1, which is

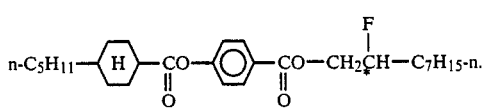

30. A compound according to claim 1, which is

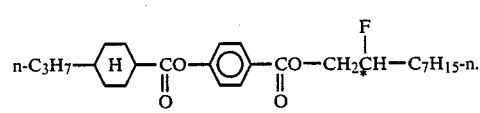

31. A compound according to claim 1, which is

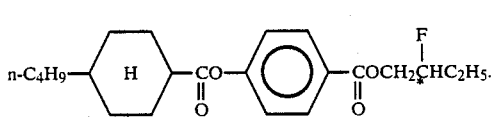

32. A compound according to claim 1, which is

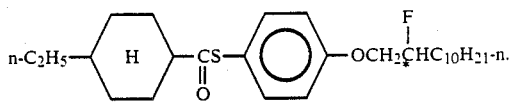

33. A compound according to claim 1, which is

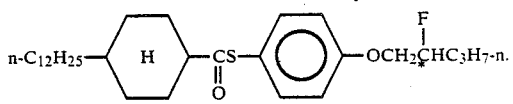

34. A compound according to claim 1, which is

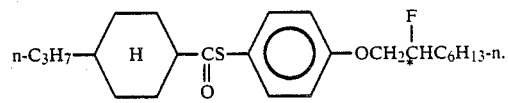

35. A compound according to claim 1, which is

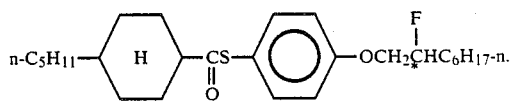

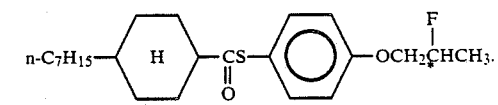

36. A chiral smectic liquid crystal composition, comprising at least two mesomorphic compounds including an optically active mesomorphic compound represented by the formula (I) according to claim 1.

37. A composition according to claim 36, which comprises the optically active mesomorphic compound represented by the formula (I) and another optically active mesomorphic compound or ferroelectric liquid crystal.

38. A composition according to claim 36, which comprises the optically active mesomorphic compound represented by the formula (I) and a non-chiral mesomorphic compound.

39. A liquid crystal device, comprising: a pair of substrates and a chiral smectic liquid crystal composition according to claim 36 disposed between the substrates.

40. A device according to claim 39, wherein said substrates have an electrode and an alignment control film.

41. A device according to claim 39, which further comprises a means for applying an AC electric field to the electrodes.

* * * * *